United States Patent [19]
Steele et al.

[11] 3,962,182
[45] June 8, 1976

[54] IMIDE OXIRANE REACTIONS

[75] Inventors: Roger B. Steele, Fair Oaks; Arthur Katzakian, Jr.; Joseph J. Scigliano, both of Sacramento; Edward E. Hamel, Placer County, all of Calif.

[73] Assignee: Aerojet-General Corporation, El Monte, Calif.

[22] Filed: July 12, 1974

[21] Appl. No.: 487,956

Related U.S. Application Data

[62] Division of Ser. No. 308,611, Nov. 21, 1972, Pat. No. 3,838,101.

[52] U.S. Cl.............................. 260/47 EN; 260/2 BP; 260/2 N; 260/49; 260/59 EP; 260/78 SC; 260/257; 260/281 P; 260/309.5; 260/326 R
[51] Int. Cl.$^2$........................................... C08G 30/14
[58] Field of Search.......... 260/47, 49, 2, 59, 18 PF, 260/78.4 EP, 78 SC, 309.5, 326 R, 94.7 N, 257, 281

[56] References Cited
UNITED STATES PATENTS

| | | | |
|---|---|---|---|
| 3,346,665 | 10/1967 | Scharzer | 260/47 |
| 3,427,260 | 2/1969 | Maguet-Martin et al. | 260/2 |

*Primary Examiner*—Murray Tillman
*Assistant Examiner*—T. Pertilla

[57] ABSTRACT

This patent discloses and claims the reaction of oxirane-containing compounds with primary cyclic imide-containing compounds, at temperatures of from about 0° to 225°C, in the presence of active chromium III tricarboxylate salts which have unoccupied coordination sites.

12 Claims, No Drawings

IMIDE OXIRANE REACTIONS

This application is a divisional of U.S. Ser. No. 308,611, filed Nov. 21, 1972 now U.S. Pat. No. 3,838,101.

BACKGROUND OF THE INVENTION

Substantial interest in thermally stable polyimide, polyamideimide, and polyesterimide resins has been shown in recent years. Polyimides are characterized by high thermal stability, outstanding resistance to irradiation, to mechanical deformation at high temperatures, and to solvent attack, good hydrolytic stability, and an excellent balance of mechanical and electrical properties over a broad temperature range. Aromatic polyimides are superior to aliphatic polyimide compositions, in that they have higher heat stability.

The reaction product of pyromellitic dianhydride with bis(4-aminophenyl)ether is an example of a known aromatic polyimide having good thermal stability. This polyimide is stable to over 500°C in vacuum or inert atmospheres, stable for over one year when stored in air at 275°C, retains toughness after one year in boiling water, and retains flexibility after 40 days exposure to a thermal neutron flux of $10^{13}$ neutrons/cm$^2$/sec at 175°C. The only known solvent for this polyimide is fuming nitric acid. The mechanical properties of glass reinforced composites using polyimide resins are generally good. Some such composites retain their flexural strength at 600°F after extended aging at 600°F and 100 hours at 700°F in air. Commercially available polyimide glass cloth reinforced composites have been reported to retain mechanical properties after more than 10,000 hours storage at 400° and 500°F in air. Polyamideimides are structurally similar to polyimides, but contain amide linkages to enhance processing characteristics. Polyesterimides exhibit good physical and electrical properties at high temperatures and a 20,000 hour service life at 230°C. The thermal and oxidative stabilities of such polymers are somewhat less than those of the best polyimides, but are still far superior to other current thermally stable polymers.

Polyimides, polyamideimides, and polyesterimides reported in the literature are prepared by either (1) melt or fusion techniques or (2) cyclization of soluble polyamic acid precursors. Regardless of the approach used by-products are formed, volatile or otherwise. Diamines and tetraacids or diamines and diacid/diesters can be reacted by melt or fusion techniques to produce meltable polymeric polyimides wherein the backbone contains the imide linkages through the following route:

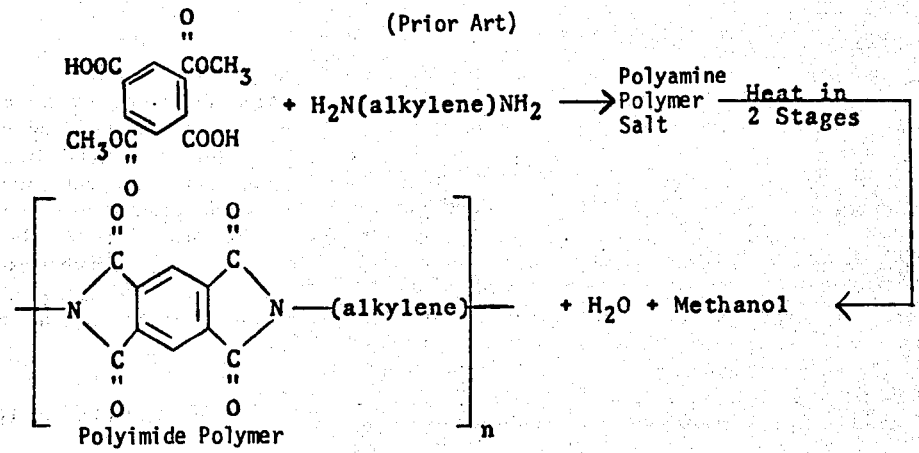

While here the Diacid/Diester is used, the tetraacid gives the same desired end product.

A more general method for the preparation of aromatic polimides and various alipatic polyimides is now in wide use. This method involves the synthesis of a soluble polyamic acid, which can be converted to the polyimide by heating at elevated temperature.

These polyamic acids are prepared by the reaction of a dianhydride with a diamine, as shown below in Prior Art Reaction IIA.

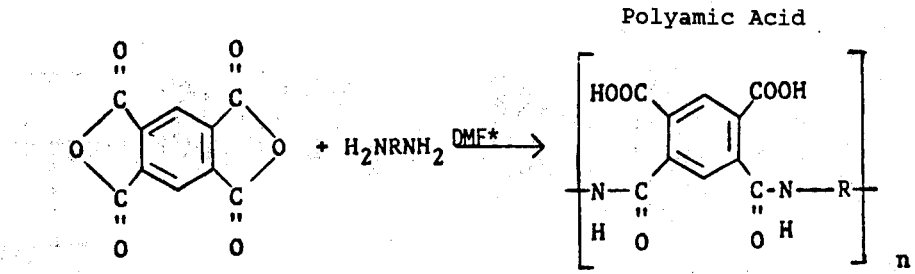

First the polyamic acid solution is heated to remove solvent, and then elevated in temperature to about 300°C, at which complete cyclization occurs to form an insoluble polyimide and water.

Reaction IIB
(Prior Art)

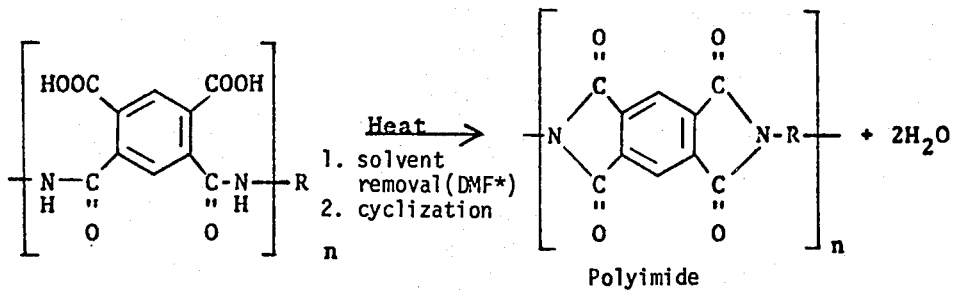

*Dimethylformamide

R in IIA and IIB is an alipathic group from 1–20 carbon atoms.

According to the present invention, it has been discovered that imide-oxirane reaction products can be produced by the reaction of primary cyclic mono, di- and polyfunctional imides with oxirane compounds in the presence of active chromium III salts having unoccupied coordination sites. These reaction proceed rapidly at temperatures above about 0°C, while state of the art polyimide preparation techniques require temperatures of at least about 300°C. In the instant invention there is no production of water or any other by-product.

The reactions of the instant invention may utilize either monofunctional or difunctional or higher functionality oxiranes and monofunctional, difunctional or higher functionality cyclic primary imides. The reaction is illustrated here by the use of a primary cyclic diimide with a difunctional oxirane, in the presence of an active chromium III catalyst.

where R is aliphatic, aromatic, cyclo aliphatic, aralkyl, alkaryl as well as the above moieties with non-reactable substituents such as halogens, cyano, ether, ester, amide, imide, etc., thereupon and y is 1 or 0, and n is an integer of at least 2.

Since no by-products are evolved, these polymers are amenable to standard bag molding techniques for preparing fiber reinforced structures, thus reducing fabrication costs and opening the application of these polymers to large structures. These polymers are also useful as adhesives, where the absence of by-products eliminates the need for high pressure for bonding. They can also be used in simple potting operations where only heat is required to obtain even large castings for encapsulation of electronic components.

SUMMARY OF THE INVENTION

In brief, this invention comprises the method of reacting oxirane-containing compounds with imide-containing compounds, at from about 0° to 225°C, in the presence of active chromium III tricarboxylate salts which have unoccupied coordination sites.

Reaction III

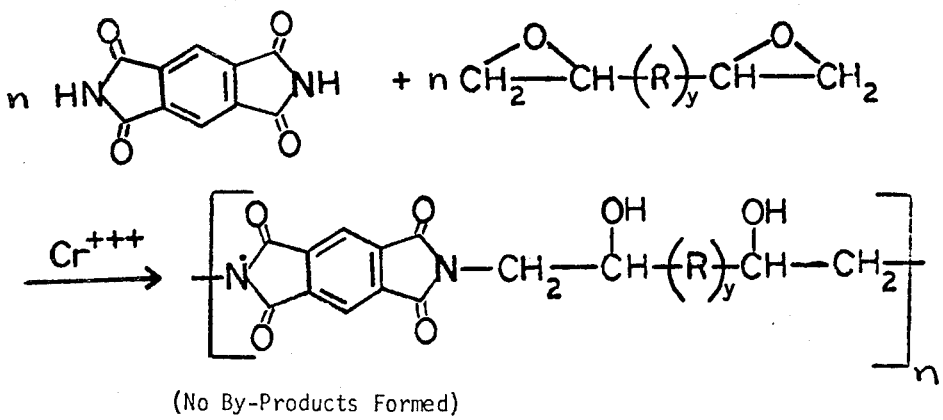

(No By-Products Formed)

The major object of the present invention is to provide a novel chromium catalyst for use in the reaction of oxirane oxygen compounds and imide moieties.

Another major object of the invention is to provide a novel chromium catalyst for the preparation of polyimides, and polyesterimides at lower temperatures without the evolution of volatiles.

More particularly, it is an object of our present invention to provide a novel chromium catalyst for the reaction of imide-oxirane systems at temperatures below about ambient.

These and other objects and advantages of this invention will be apparent from the more detailed description which follows.

Chromium salts having oxidation states of chromium varying between one and six are known. Chromium III is the most stable and important oxidation state of the element and has six coordination sites arranged in an octahedral configuration about the central ion. The coordination sites of chromium III account for the existence of stable complex ions such as the hexaaquochromium ion and the hexaaminochromium ion. In both of the above examples the water and ammonia, commonly called ligands, occupy the six coordination sites of chromium III. Ligands may be electrically neutral, as in the cases of water and ammonia, or negatively charged as in the case of the cyanide ion which gives rise to the negatively charged hexacyanochromium ion. Chelating agents, such as the acetylacetonate anion, also form exceedingly stable chromium chelates in which all of the chromium III coordination sites are occupied. The removal of the above-mentioned ligands from the chromium III ion or the displacement of these ligands by other ligands is an extremely difficult and slow process. It is largely because of this kinetic inertness that so many complex chromium III species can be isolated and that they persist for relatively long periods of time in solution, even under conditions when they are thermodynamically quite unstable. Thus, the normally occurring form of chromium III compounds is the fully coordinated state. The kinetic stability of its widely found complex coordination compounds sets the chromium III ion apart from most other trivalent transition metal ions. We have found that the commonly occurring fully coordinated chromium III carboxylates are poor catalysts for imide-oxirane reactions. Quite surprisingly, however, we have found that chromium III in an uncoordinated state is a superior catalyst for such reactions.

The preferred chromium III tricarboxylate salts are those in which three of the six coordination sites on chromium III are unoccupied and are thus available to participate in catalysis of the imide-epoxy reaction. Three chromium III coordination sites are occupied by the carboxylate anions to produce a neutral molecule; the remaining three sites being unoccupied. The alkyl side chain of the carboxylate anions may be adjusted in order to effect the necessary solubility in various reaction media necessary for efficient catalysis.

While not bound by any theory, it is believed that the catalysis of the imide-epoxy reaction by $Cr(OCOR)_3$ is based on the transient occupation of the available chromium III coordination sites by an epoxide and an imide molecule. This unique activated complex places the epoxide and the imide in the proper environment for reaction to occur. The catalyst is regenerated and thus is able to participate in further reactions. Reference is made to the equation of Reaction IV below.

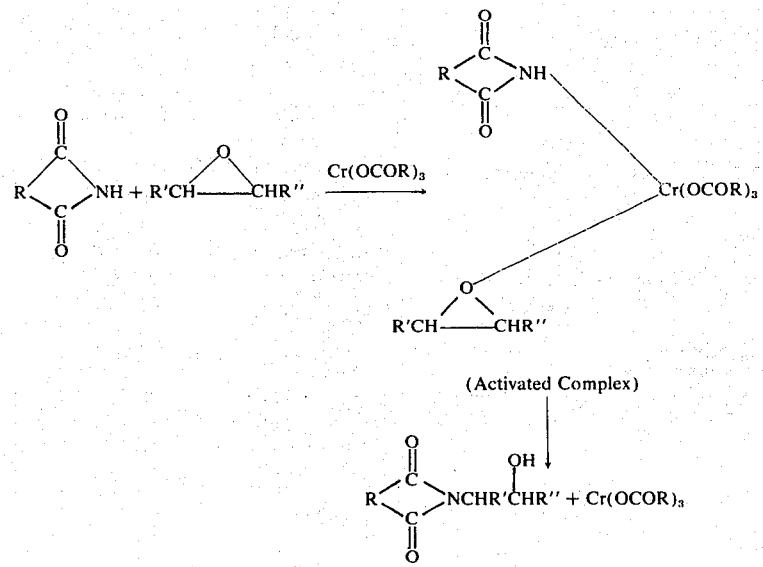

R, R' and R'' have the same significance here as R does in Reaction III, and that R, R' and R'' may be the same or various combinations of those moieties represented by R in Reaction III.

DESCRIPTION OF PREFERRED EMBODIMENTS

The active chromium III salt preparation is illustrated as follows. A solution of 120g (3.0 moles) of sodium hydroxide was dissolved in 500 ml of distilled water. 2-Ethylhexanoic acid (491g, 3.3 moles) was added with stirring to form sodium 2-ethylhexanoate. In a separate container, 200g (0.5 mole) of chromium nitrate nonahydrate was dissolved in 500 ml of distilled water. The chromium nitrate solution was slowly added to the sodium 2-ethylhexanoate solution with good stirring. When the addition was complete, 500 ml of hexane were added and stirring was continued for 10 minutes. The layers were separated and the hexane layer containing the aquated chromium III tri-2-ethylhexanoate was washed with dilute sodium hydroxide solution, water, dilute sodium carbonate solution and finally with distilled water. The hexane solution was then dried over anhydrous magnesium sulfate. Most of the hexane was removed under reduced pressure and the resulting concentrate was slowly added to 500 ml of acetone. The resulting blue granular solid was filtered and air dried to yield 130g (54%) of aquated chromium tri-2-ethylhexanoate. Molecular weight determination indicated that the compound is polymeric in nature, probably due to the oxygen bridging of chromium atoms.

Anal. Calcd for $C_{24}H_{51}O_9Cr$: C, 53.8; H, 9.6; Cr, 9.7. Found: C, 53.2; H, 8.7; Cr, 9.4.

Azeotropic data indicated three molecules of water per chromium atom.

A stock solution of 5.0g of aquated chromium tri-2-ethylhexanoate and 2.5g of 2-ethylhexanoic acid in chloroform was prepared. Ten-ml aliquots of this solution were transferred to each of ten 50-ml volumetric flasks and placed in a 140° oven for 0 (control), 0.5, 1.5, 3 and 6 hours. After each time interval two of the flasks were removed from the oven. One was diluted to the mark with carbon tetrachloride and the conversion from aquated to active chromium tri-2-ethylhexanoate was determined by measuring the absorption intensity of the solution at 2,750 millimicrons. It was determined that fully aquated chromium tri-2-ethylhexanoate absorbs strongly at 2,750 millimicrons while the active deaquated chromium compound does not absorb at this wavelength. The conversion from catalytically inactive fully coordinated aquo chromium tri-2-ethylhexanoate to the active form is about 44% complete after 6 hours. Further heating at 200°C with the addition of 2-ethylhexanoic acid raises the conversion to about 90%.

Once the necessary coordination sites on chromium III have been freed for catalyst participation, care must be taken to insure catalyst activity during the reaction. Inert solvents such as benzene, toluene, methylisobutyl ketone etc., are acceptable. Electron donating solvents such as methanol, ethanol, dimethylformamide, dioxane and tetrahydrofuran, however, were found to retard catalysis at temperatures on the order of room temperature. These electron donating solvent molecules tend to strongly solvate the chromium III metal ion, blocking the transient residence of the imide-epoxy reagents on these sites and thus preventing reaction catalysis.

In general, the chromium III tricarboxylate salts are prepared by the reaction of an aquated inorganic chromium III salt such as aquated chromium nitrate with three moles of sodium carboxylate.

Reaction V

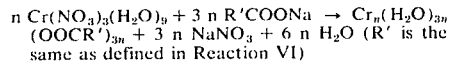
n Cr(NO₃)₃(H₂O)₉ + 3 n R'COONa → Cr<sub>n</sub>(H₂O)<sub>3n</sub>(OOCR')<sub>3n</sub> + 3 n NaNO₃ + 6 n H₂O (R' is the same as defined in Reaction VI)

The chromium III salt obtained by this method is catalytically inactive since the six chromium III coordination sites are occupied both by the water and carboxylate anions. In order to produce the active catalyst, the aquated form must be subjected to a high temperature, acid catalyzed process in which the coordination sites are freed of water.

Reaction VI

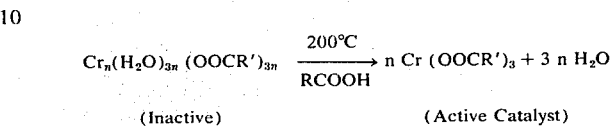

(Inactive)   (Active Catalyst)

In the above equations, R' is a monovalent organic radical such as alkyl, aryl, alkaryl or aralkyl, and preferably contains from 1 to about 20 carbon atoms.

The anion (negatively charged) portion of the catalyst is also critical to its activity in the sense that it may not cause complete coordination. For example, if the carboxylate anion is replaced by the acetylacetonate anion the resulting chromium III acetylacetonate is catalytically inactive under the low temperature range of our test conditions. The reason for this is that the acetylacetonate groups effectively occupy all of the chromium III coordination sites.

Reaction VII

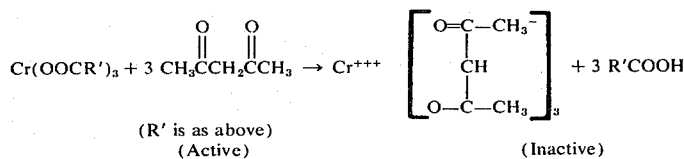

(R' is as above)
(Active)   (Inactive)

The epoxide-containing compositions capable of using our novel catalyst comprise organic materials having reactive epoxy groups.

The invention is applicable to any oxirane oxygen compounds including ethylene oxide, 1,2-propylene oxide, 1,2-butylene oxide, 2,3-butylene oxide, 1,2-epoxyhexane, cyclohexane oxide, cyclopentene oxide, cyclopentadiene monoxide and the like. The invention is particularly adapted to the reaction of any epoxyalkanes or epoxycycloalkanes, typically containing from 2 to about 20 carbon atoms, with organic imides. Other oxiranes utilizeable include styrene oxide, 1,2,3,4-diepoxy butane, 1,2;5,6,-diepoxy hexane, diepoxide of divinyl benzene, and the like.

The epoxide materials for use in the invention include organic materials having a plurality of reactive 1,2-epoxy groups. These polyepoxide materials can be monomeric or polymeric, saturated or unsaturated, aliphatic, cycloaliphatic, aromatic or heteroyclic, and they may be substituted if desired with other substituents besides the epoxy groups, e.g., hydroxyl groups, ether radicals, halogen atoms, and the like. The more common types of polyfunctional oxiranes are derived from the reaction of epichlorohydrin or other halohydrins with 2,2-di(p-hydroxyphenyl) propane, the glycidyl ether of mononuclear di- and trihydroxyl phenols (resorcinol, hydroquinone, pyrocatechol, saligenin and phloroglucinol), the glycidyl ether of other polyhydroxy phenols (Bisphenol F, trihydroxyldiphenyl dimethyl methane, 4,4' - dihydroxy biphenyl, tetrakis hydroxyphenyl ethane, long-chain bisphenols, dihydroxy diphenyl sulfone, and Novolacs), the glycidyl ethers of polyalcohols (ethylene glycol, 1,4-butanediol, glycerol, erythritol, and polyglycols), and the epoxylated cyclic and straight chain olefins (vinyl cyclohexene, dicyclohexene carboxylate, and polybutadienes). These and many other epoxy resins are commercially available.

The present invention is also applicable to epoxy resins which may be reacted in the presence of the active trivalent chromium catalysts with the imides. Typical epoxy resins suitable in the practice of the present invention are those disclosed in U.S. Pat. Nos. 2,500,600 and 2,324,433 as well as those set forth in our co-pending application, Ser. No. 218,015 filed Jan. 14, 1972 in the name of Katzakian, et al, the disclosures of which are expressly incorporated herein by reference. While not limited thereto, the epoxy resins of the present invention normally have epoxy equivalent weight values of from about 100 up to 4,000 or higher.

As 1:2-epoxy compounds to be used in the present invention there may be used monoepoxides, such as butylglycide, phenylglycide, cresylglycide, 3:4-epoxy-tetra-hydrodicyclopentadienol - 8, 3:4-epoxy-hexahydrobenzal glycerol or 3:4-epoxy-cyclohexane-1:1-dimethanol-acrolein acetal. Preferred use is made of 1:2-epoxy compounds having an epoxide equivalence greater than 1, that is to say compounds containing x groups of the formula,

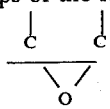

calculated from the average molecular weight, where x is a whole fractional number greater than 1.

According to this invention the oxiranes can be reacted with any primary cyclic imide. The imide may be mono-, or polyfunctional and may be a low molecular weight monomeric material or an intermediate molecular weight liquid prepolymeric material, this latter suitably having a molecular weight from 1,000 to 5,000.

The 1:2-epoxide groups may be either terminal or inner ones. Particularly suitable terminal 1:2-epoxide groups are 1:2-epoxyethyl or 1:2-epoxypropyl groups; the later may be linked to an oxygen atom, that is to say they are glycidylether or glycidylester groups. Compounds with inner epoxide groups contain at least one 1:2-epoxide group in an aliphatic chain

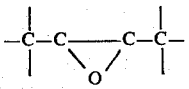

or in a cycloaliphatic ring.

As epoxy compounds containing an inner 1:2-epoxide group there are suitable expoxidised diolefines, dienes or cyclic dienes, such as 1:2:5:6-diepoxyhexane, 1:2:4:5-diepoxycyclohexane, dicyclopentadiene diepoxide, dipentene diepoxide and more especially vinyl-cyclohexene diepoxide; epoxidized, diolefinically unsaturated carboxylic acid esters, such as methyl-9:10:12:13-diepoxystearate; or the dimethyl ester of 6:7:10:11-diepoxyhexadecane-1:16-dicarboxylic acid. Furthermore, there may be mentioned epoxidized mono-, di- or poly-ethers, mono-, di or poly-esters, mono-, di- or poly-acetals containing at least one cycloaliphatic 5-membered or 6-membered ring, to which at least one 1:2-epoxide group is linked. Suitable compounds of this kind are those of the following formulae

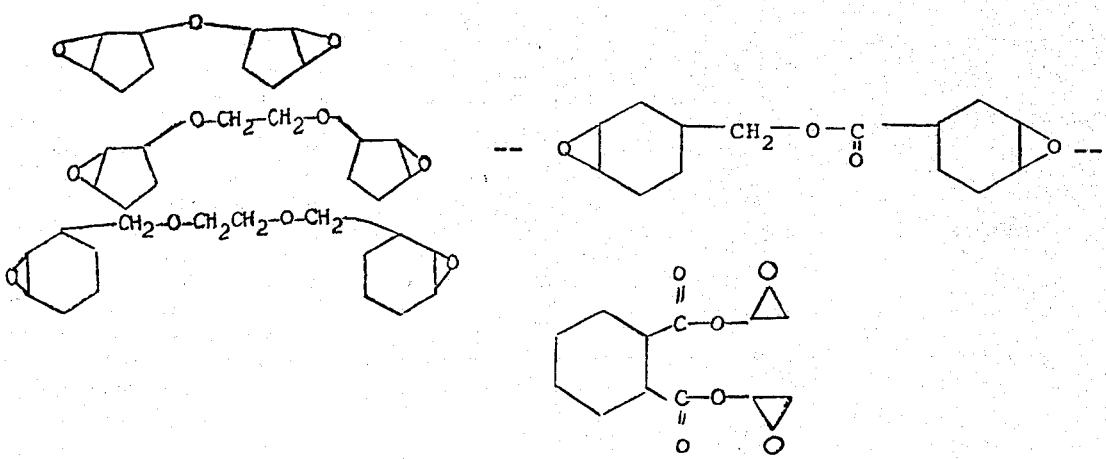

A widely used class of polyepoxides which can be catalyzed in reaction with anhydrides according to the practice of the present invention encompasses the epoxy polyethers obtained by reacting a halogen containing epoxide or dihalohydrin, such as epichlorohydrin, epibromohydrin, epiiodihydrin, 3-chloro-1,2, epoxyoctane, and the like with either a polyhydric phenol or a polyhydric alcohol.

Among the polyhydric phenols which can be used in preparing these polyethers are dihydric phenols represented by the general formula:

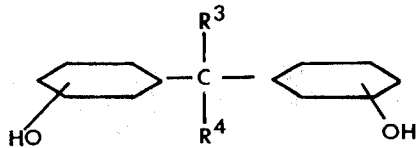

wherein the phenolic hydroxy groups may be in one of the 2,2'; 2,3'; 2,4'; 3,3'; 3,4'; or 4,4' positions on the aromatic nuclei, and each of R³ and R⁴ represent hydrogen, an alkyl group, such as methyl, ethyl, propyl, isopropyl, butyl; sec-butyl, tert-butyl, pentyl, isopentyl, hexyl, isohexyl, and the like; a cyclo (lower)-alkyl group, such as a cyclohexyl or substituted cyclohexyl group, e.g., methyl-, ethyl-, propyl-, butyl-, pentyl- and hexyl-substituted cyclohyxyl, or an aromatic group, such as phenyl, tolyl, xylyl, and the like. In addition, the phenolic rings may have other substituents besides the hydroxyl group, for example, lower alkyl groups containing from 1 to 4 carbon atoms, i.e., methyl, ethyl, propyl, isopropyl, butyl, secbutyl and tert. butyl groups, halogen atoms, i.e., fluorine, chlorine, bromine or iodine, and the like.

An illustrative listing of dihydric phenols falling within this general formula includes 4.4'-dihydroxydiphenyldimethylmethane (bisphenol A), 2,4'-dihydroxydiphenylethylmethane, 3,3' - dihydroxydiphenyldiethylmethane, 3,4' -dihydroxydiphenylmethylpropylmethane, 2,3' - dihydroxydiphenylethylphenylmethane, 4,4' -dihydroxydiphenylpropylphenylmethane, 4,4' -dihydroxydiphenylbutylphenylmethane, 2,2' -dihydroxydiphenylditolylmethane, 4,4' -dihydroxyphenyltolylmethylmethane, 4.4-dihydroxydiphenylmethane (bisphenol F), and the like.

Other polyhydric phenols which may also be co-reacted with halohydrins to provide these epoxy polyethers are such compounds as resorcinol, hydroquinone substituted hydroquinones, and polyhydric phenols having two hydroxylaryl groups separated by an aliphatic chain of at least six carbon atoms in length, said chain being attached by carbon-to-carbon bonding to nuclear carbon atoms of the hydroxylaryl groups. Members of this latter class of polyhydric phenols can be conveniently obtained by condensing phenol substituted with an aliphatic side chain having one or more olefinic doubls bonds positioned therein, thus providing the required number of separating atoms between the two hydroxyphenyl groups of the resulting polyhydric phenol. Cardanol, obtainable in known manner from cashew nut shell liquid, is a convenient source of phenols containing such side chains.

The monomer products produced by this method from dihydric phenols and epichlorohydrin may be represented by the general formula, e.g.,

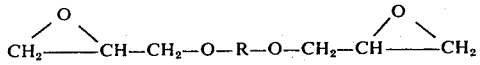

wherein R represents a divalent hydrocarbon radical of the dihydric phenol alcohol. The polymeric products will generally not be a single simple molecule but will be a complex mixture of glycidyl polyethers of the general formula:

wherein R is a divalent hydrocarbon radical of the dihydric phenol and n is an integer of the series 0, 1, 2, 3, etc. While for any single molecule of the polyether n is an integer, the fact that the obtained polyether is a mixture of compounds causes the determined value for n to be an average which is not necessarily zero or a whole number. The polyethers may in some cases contain a very small amount of material with one or both of the terminal glycidyl radicals in hydrated form.

The aforedescribed preferred glycidyl polyethers of the dihydric phenols may be prepared by reacting the required proportions of the dihydric phenol and the epichlorchydrin in an alkaline medium, as per U.S. Pat. No. 2,768,153.

Among the polyhydric alcohols which can be co-reacted with a halogenated oxirane, such as epihalohydrin to provide these epoxy polyethers are such compounds as ethylene glycol, propylene glycols, butylene glycols, pentane diols, bis (4-hydroxycyclohexy) dimethylmethane, 1,4-dimethylolbenzene, glycerol, 1,2,6-hexanetriol, trimethylol propane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyvinyl alcohol, polyhydric thioethers such as 2,2'-dihydroxydiethyl sulfide, 2'2', 3,3'-tetrahydroxydipropyl sulfide and the like, mercapto alcohols such as a-monothioglycerol, a,a'-dithioglycerol, and the like, polyhydric alcohol partial esters such as monostearin, pentaerythritol monoacetate and the like, and halogenated polyhydric alcohols such as the monochlorohydrins of glycerol, sorbitol, pentaerythritol and the like.

The resulting reaction products may contain free terminal carboxyl groups or terminal hydroxyl groups and terminal epoxy groups, and will vary in molecular weight depending on the reactants employed, the relative amounts thereof, and the extent to which the reaction is carried out. Still another class of polyepoxides includes the epoxy-containing monomers which also contain at least one polymerizable double bond. Such monomers can be polymerized through their double bonds in known manner, e.g., in bulk or in solution in an inert organic solvent such as benzene and the like, preferably by heating in the presence of oxygen or a peroxide catalyst but, in the absence of alkaline or acidic catalysts, leaving the epoxy groups unaffected and, therefore, regularly or randomly dispersed along the polymer chains, if such is desired. Among such ethylenically unsaturated epoxy-containing monomers are vinyl 2,3 glycidyl ether, allyl 2,3-glycidyl ether, methallyl 2,3-glycidyl ether, methallyl 3,4-epoxybutyl ether, glycidyl acrylate, glycidyl methacrylate, 2,3-epoxypropyl crotonate, vinyl cyclohexane monoxide, 4-glycidyloxystyrene and the like. Another group of polyepoxides include the epoxy esters of polybasic acids such as diglycidyl phthalate and diglycidyl adipate, diglycidyl tetrahydrophthalate, diglycidyl maleate, epoxidized dimethallyl phthalate and epoxidized dicrotyl phthalate.

Among the monomeric polyepoxides which can be reacted with anhydrides per the present invention are the di- and triepoxides represented by the general formula:

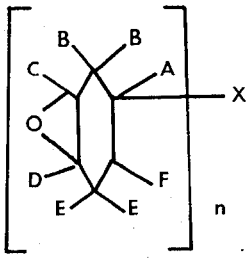

wherein A through F represent hydrogen or an alkyl group preferably a lower alkyl group having from 1 to 4 carbon atoms, inclusive, such as methyl, ethyl, propyl, n-butyl and the like, and X represents a divalent radical which can be:

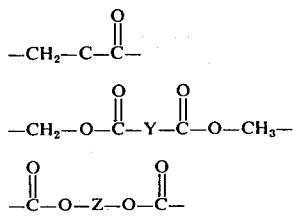

in which case $n$ equals 2, or a trivalent radical which can be

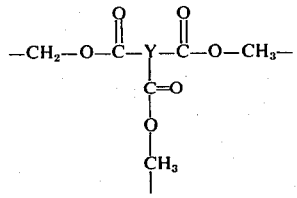

or

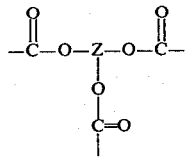

in which case $n$ equals 3, with Y representing an aliphatic or aromatic hydrocarbon radical containing from 2 to 12 carbon atoms, inclusive, and Z representing a lower aliphatic hydrocarbon radical or a lower oxyalkylene group, e.g., alkylene-o-alkylene- and the like. Included among such di- and triepoxides are 3,4-epoxycyclohexylmethyl 3,4-epoxy-cyclohexanecarboxylate, 3,4-epoxy-6-methylcyclohexylmethyl, 3,4-epoxy-6-methylcyclohexanecarboxylate, bis(3,4-epoxycyclohexylmethyl) maleate, bis(3,4-epoxy-6-methylcyclohexylmethyl)-succinate, ethylene glycol bis(3,4-epoxycylohexanecarboxylate), 2-ethyl-1,3-hexanediol bis(3,4-epoxy-6-methylcyclohexanecarboxylate), tris(3,4-epoxycyclohexylmethyl) 1,2,4-hexanetricarboxylate, glyceryl tris(3,4-epoxy-6-methylcyclohexanecarboxylate) and the like.

Other monomeric polyepoxides which can be used include dicyclopentadiene dioxide, epoxidized triglycerides such as epoxidized glycerol trioleate, epoxidized glycerol trilinoleate, the diacetate of epoxidized glycerol trilinoleate and the like, 1,8-bis-(2,3-epoxypropoxy) octane; 1,4 - bis(2,3 - epoxypropoxy) cyclohexane; 1,4 - bis(3,4-epoxybutoxy) - 2 - chlorocyclohexane; 1,3-bis(2,3-epoxypropoxy) benzene; 1,4 - bis(2,3-epoxypropoxy) benzene; 1,3-bis (2 - hydroxy-3,4-epoxybutoxy)benzene; 1,4-bis(2-hydroxy-4,5-epoxypentoxy) benzene; 1,3 - bis(4,5-epoxypentoxy)-5-chlorobenzene; 4,4'-bis(2,3 - epoxypropoxy) diphenyl ether; and epoxy esters of polybasic acids such as diglycidyl succinate, diglycidyl adipate, diglycidyl maleate, digycidyl phthalate, diglycidyl hexachloroendomethylenetetrahydrophthalate and diglycidyl 4,4'-isopropylidenedibenzoate, and the like.

Furthermore, there are suitable polyglycidylesters accessible by reacting a dicarboxylic acid with epichlorohydrin or dichlorohydrin in the presence of an alkali; such polyesters may be derived from aliphatic dicarboxylic acids, such as oxalic, succinic, glutaric, adipic, pimelic, suberic, azelaic, sebacic acid, or more especially from aromatic dicarboxylic acids, such as phthalic, isophthalic, diphenylortho: ortho'-dicarboxylic acid, ethyleneglycol-bis-(paracarboxyphenyl)-ether or the like. as examples there may be mentioned diglycidyl adipate and diglycidyl phthalate.

Many of those polepoxides, and particularly those which are polymeric can be conveniently referred to in terms of epoxy functionality, i.e., the average number of epoxy groups per molecule in the polyepoxide material. Where the polyepoxide is monomeric and all of its epoxy groups are intact, its epoxy functionality will be represented by an integer, usually 2 or greater. However, where the polyepoxide is polymeric its epoxy functionality will usually be represented by a fractional value of at least about 1.0 or greater, e.g., 1.5, 1.8, 2.3, and the like, since the polymer will usually contain molecules of different molecular weight and can also contain some monomeric polyepoxide or have some of its epoxy groups dehydrated or otherwise reacted.

Flame-inhibiting properties in the final product may be achieved by using 1.2-epoxy compounds that additionally contain halogen, more especially chlorine or bromide. The following examples of such halogen-containing epoxy compounds may be mentioned.

Diglycidylethers of chlorinated bisphenols, 2:3-dichloro-1:4 butanediol diglycidylether, 2:3-dibromo-1:4-butanediol diglycidyl ether, 2:2. 3:3-tetrachloro-1:4-butanediol diglycidylether.

It is to be seen that the number of oxirane compounds suitable for use in this reaction with carboxylic acids in the presence of the catalyst compositions forming part of this invention is quite large. Some of these have been recited above, others will be recited below. In any event those not specifically recited, but which are utilizeable are set forth in "Epoxy Resins, Chemistry and Technology", May and Tanaka, c 1973 Marcel Dekker, Inc., at Chapter 2 pages 9 to 106 inclusive; "Handbook of Epoxy Resins", Lee and Neville, c 1967 McGraw-Hill, Inc., at Appendix 4–1 and 4–2. Still other nonenumerated types of oxiranes are recited in U.S. Pat. Nos. 3,296,208; 3,449,353, 3,542,803, 3,629,263, 3,676,456, 3,679,681, 3,697,539, 3,714,198, 3,772,326, 3,779,949, 3,784,525, and 3,784,584. These book sections and the disclosures of these patents are herein incorporated by reference.

Utilizable cyclic imides for the practice of this invention, are those of the formulae:

A.

$$\left[ L - \underset{R}{\overset{Q}{\vert}} - L \right]_m$$

and

B.

$$Z - \left[ \underset{(L)}{\overset{O\ O}{\underset{\Vert\ \Vert}{R - R_3}}} \right]_n - T$$

wherein L represents an imide moiety $$\begin{matrix} -\overset{O}{\underset{\Vert}{C}} \\ -\underset{\Vert}{C} \\ \overset{\Vert}{O} \end{matrix} \!\!> \! NH,$$

$m$ is a number of either 0 or 1, and n is at least 2. When $m = 0$, R represents a moiety selected from the group consisting of:

[structures shown]

when $m = 1$, R represents a moiety selected from the group consisting of:

[structures shown]

X represents a group selected from the group consisting of:

$$-O-,\ -S-,\ -\underset{H}{\overset{H}{\underset{\vert}{\overset{\vert}{C}}}}-,\ -\underset{CH_3}{\overset{CH_3}{\underset{\vert}{\overset{\vert}{C}}}}-,\ -\overset{O}{\underset{\Vert}{C}}-,\ -\overset{O}{\underset{\underset{O}{\Vert}}{\underset{\Vert}{S}}}-,\ -\underset{CH_3}{\overset{CH_3}{\underset{\vert}{N}}}-,\ -\underset{CH_3}{\overset{O}{\underset{\vert}{\overset{\Vert}{P}}}}-$$

Each $R_2$ represents the same or different group selected from the group consisting of alkyl ($C_1$ to $C_{10}$), alkenyl ($C_1$ to $C_{10}$), cycloalkyl wherein there are 4 to 8 carbon atoms in the ring, aryl, alkaryl, and aralkyl;

Q represents those valences on R which, while understood to be filled with hydrogen atoms are available for substitution by non-interfering groups selected from among:

—F, —Cl, —BR, —I, —OH, —NO$_2$, —SO$_2$CH$_3$, —OCH$_3$, —COOH, and —COOCH$_3$, —CN, $$-\overset{O}{\underset{\Vert}{C}}NH_2,$$

—CO—N(CH$_3$)—CO—, and the like;

Z represents either, a group derived from an ionic or free radical polymerization initiator, or H;

T represents a terminal group derived from an ionic or free radical polymerization initiator, when Z is not H; or when Z is H, a chain terminator group or H;

$R_3$ represents a moiety selected from the group consisting of

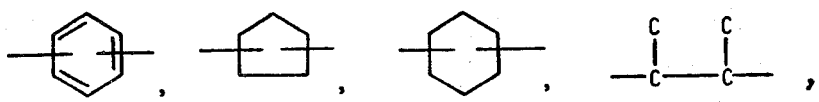

and wherein each bond depicted in the groups and moieties of R, X, $R_2$, $R_3$, and Q actually represents a half-bond in order to best illustrate points of attachment.

All mono and polyfunctional primary imides, reported in the literature, as well as any others that are primary imides which would be derived from carboxylic acid anhydrides are contemplated for use herein.

These materials can be monomeric or polymeric, saturated or unsaturated, aliphatic, cycloaliphatic, aromatic or heterocyclic, and they may be substituted if desired with other substituents, é.g. hydroxyl groups, either radicals, halogen atoms, and the like.

Typical among the cyclic anhydrides that can be converted to imide compounds are the following monoanhydrides; phthalic anhydride, methylendomethylene tetrahydrophthalic anhydride, succinic anhydride, dodecenylsuccinic anhydride, maleic anhydride, hexahydrophthalic anhydride, hexachloro-endomethylene tetra-hydrophthalic anhydride, endomethylene tetrahydrophthalic anhydride or mixtures thereof.

The process for accomplishing same is readily known in those participating in this art, by the addition of ammonia, followed by dehydration.

Other well known anhydrides that are convertable to imides are the polyfunctional cyclic anhydrides. Among these, mention may be made of pyromellitic tetracarboxylic acid dianhydride, benzophenone tetracarboxylic acid dianhydride, cyclopentane tetracarboxylic acid dianhydride, diphenylether tetracarboxylic acid dianhydride, and the hexacarboxylic acid trianhydrides of benzene, and of cyclohexane.

Another class of imides utilizeable are the linear mono and di functional primary imides prepared for instance by the reaction of acid halides such as acetyl chloride, dimer acid chloride, formyl bromide, adipyl chloride, benzyl iodide, sebacicyl dichloride, tetraphthalcyl chloride and the like with primary imides such as foramide, acetamide, benzamide, tolylamide, adipic acid diamide, and all other amides formed from mono and polyfunctional carboxylic acids, saturated and unsaturated, and which may contain other noninterfering substituents thereupon. Primary amides of fatty acids can also be converted to imides in this manner. Typical of such fatty acids which can be converted to imides are stearic, caprylic, linoleic, palmitic, and oleic and the like.

Another class of imides utilizeable herein are those prepared from unsaturated cyclic or linear anhydrides such as maleic anhydrides and substituted maleic anhydrides, e.g., chlormaleic, and itaconic, in a Diels-Alder reaction with at least one conjugated diene, e.g. 1,3-cyclopentadiene, 1,3-butadiene. Such anhydrides from which the imides corresponding thereto are readily formed, are described in U.S. Pat. No. 3,271,476, wherein 1:5-bis (cyclcopentadienyl) pentane is reacted with maleic anhydride. Compounds of this calss fall within the scope of formula (B).

Still another class of imides are those derived from the polymerization of unsaturated cylic or linear anhydrides with monomers which contain at least one polymerizeable double bond. Such monomers can be polymerized through their double bonds in known manners, with known catalysts. Suitable comonomers for copolymerization with these anhydride monomers include styrene, acrylonitrile, methacrylonitrile, methyl acrylate, ethyl acrylate, methyl methacrylate, vinyl chloride, vinylidene chloride, vinyl acetate, diallyl phthalate, and the like. These also are within the scope of Formula (B).

It is seen that the imide can be reacted with the polymerizeable double bond monomer to form the high molecular weight polyfunctional imides, directly, or the anhydride from which the imide will be prepared can be reacted with the unsaturated compound, first, followed by the conversion to the imide form by known techniques.

Another class of imides utilizeable herein are those prepared from the reaction of two moles of a diimide and one mole of dihalide of a dicarboxylic acid. The preparation of such products is set forth in U.S. Pat. No. 3,346,665 issued to Schwarzer, said patent being incorporated herein by reference.

While any mono or polyfunctional imide compound can be utilized in this invention, particularly good results can be obtained when the imide compound utilized is a polyfunctional cyclic, saturated or unsaturated aliphatic or aromatic compound, such as pyromellitic diimide, and tetrahydrophthalimide, barbituric acid, adipimide, terephthaldiimide, and bis (3,4-dicarboxyphenyl)ether diimide. Typical of those of Formula A are the following when $m = 0$; succinimide, maleimide, phthalimide, 4-tetrahydrophthalimide, Δ, 4 tetrahydrophthalimide, hexahydrophthalimide, mono- and dichloromaleimide, dodecenylsuccinimide glutarimide;

and when $m = 1$;

1,2,4,5 - benzenetetracarboxylic diimide, 1,2,3,4 - cyclopentanetetracarboxylic diimide, 3,4,3',4' -diphenyl-dimethylmethanetetracarboxylic diimide, 3,4,3',4' - diphenylethertetracarboxylic diimide, 3,4,3',4' - benzophenetetracarboxylic diimide, 1,2,3,4 - butanetetracarboxylic diimide, barbituric acid.

Compounds with Q substituents are as follows:
1,4 - difluoro - 2,3,5,6 - benzenetetracarboxylic diimide, 2,2' -diphenoxy 3,4,3',4' -diphenylethertetracarboxylic diimide, 2,2' - dicyano - 3,4,3',4'- benzophenonetetracarboxylic diimide.

Imide terminated prepolymers may be prepared by the reaction of excess diimide with isocyanate terminated materials such as dimeryldiisocyanate or toluene diisocyanate (TDI). Imide terminated prepolymers can also be prepared by reaction of excess diimide with polyfunctional acid chlorides such as those of dimer or trimer acid chloride.

Compounds such as 4-carboxyphthalimide can be reacted with aliphatic diamines to produce amideimides which are, in turn, reacted with diepoxides to prepare polyamideimides. The overall reaction is as follows with the reaction of I + oxirane being carried out in the presence of the catalyst of this invention:

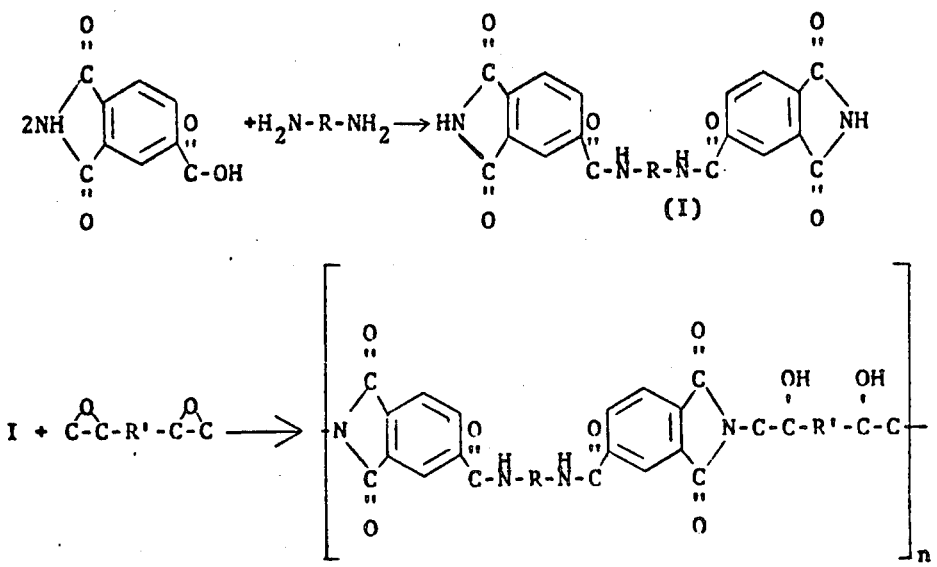

wherein R and R' are divalent organic radicals such as phenylene, ethylene, biphenylene, xylylene and the like, and n is at least 2.

In the practice of the invention, the catalytically active trivalent chromium compound is used in an effective catalytic amount, of from about 0.1 to about 10% by weight of the reactants with an epoxy resin or other oxirane oxygen compound (s) and the imide(s).

The relative amount of each reactant to be used depends to some extent upon the functionality of both as well as the precise properties desired in the final product. For tough, hard final cured products, at least part of the oxirane compound content and/or the imide compound content should have a functionality greater than two. However, since both components are well-known to those skilled in the art, the selection of these proportions does not form a part of the present invention.

EXAMPLE I

Preparation Of N-2-Hydroxyethyl Phthalimide

N-2-Hydroxyethyl phthalimide was prepared by allowing 147.2g (1.0 mole) of phthalimide to react in an autoclave with 53.0g (1.20 moles) of ethylene oxide in the presence of 1.47g (1%) of active chromium III tri-2-ethylhexanoate (COT) and 400 ml of methylisobutyl ketone (MiBK) at 160° to 165°C for two hours. On cooling, the N-2-hydroxyethyl phthalimide crystallized and was collected by filtration. A 94.7% yield of the hydroxyethyl imide was obtained. Under identical experimental conditions but in the absence of COT, the starting material was recovered unchanged.

EXAMPLE II

Preparation of N-2-hydroxyethyl Succinimide

N-2-Hydroxyethyl succinimide was prepared by reacting 49.5g (0.5 mole) of succinimide with 26.5g (0.60 mole) of ethylene oxide in the presence of 0.49g (1%) of active chromium III tri-2-ethylhexanoate and 400 ml of methylisobutyl ketone for 2 hours at 160° to 165°C in an autoclave. N-2-Hydroxyethyl succinimide was obtained by filtration in 87.5% yield. The reaction did not proceed in the absence of COT.

EXAMPLE III

Preparation of 3-(2-Hydroxyethyl)-5,5-Dimethylhydantoin 3-(2-Hydroxyethyl)-5,5-dimethylhydantoin was prepared via the reaction of 12.8g (0.1 mole) of 5,5-dimethylhydantoin with 10.6g (0.24 mole) of ethylene oxide in the presence of 0.12g (1%) of active chromium III tri-2-ethylhexanoate and 300 ml of MIBK in an autoclave for three hours at 155 to 157°C. The hydroxyethylhydantoin was obtained in 42% yield via filtration.

In the absence of the catalyst, the starting materials were recovered unchanged.

EXAMPLE IV

Preparation of 3-(2-Hydroxy-2-Phenylethyl)-5,5-Dimethylhydantoin and 3-(2-Hydroxycyclohexyl)-5,5-Dimethylhydantoin The above named compounds were prepared via the reaction of 5,5-dimethylhydantoin with styrene oxide and cyclohexene oxide in 60.5 and 34.1% yields, respectively. The reaction conditions and active chromium III tri-2-ethylhexanoate concentration were identical to those used in the preparation of 3-(2-hydroxyethyl)-5,5-dimethylhydantoin.

EXAMPLE V

Preparation of Poly($\beta$-Hydroxyalkyl Imides)

a. Reaction of Pyromelliticdiimide with Dow Epoxy Resin-332 (DER-332).*

Pyromelliticdiimide (5.4g, 0.05 equivalent) was mortar ground with 8.8g (0.05 equivalent) of DER-332 and 0.2g active chromium III trioleate. The viscous liquid cured to a rigid polymer in 15 minutes at 200°C. Under identical experimental conditions but in the absence of chromium trioleate no reaction occurred and the sample remained liquid.

*Epichlorohydrin adduct of bis-phenol A b. Reaction of Pyromelliticdiimide with Reichold Triepoxide 427–61**

Pyromelliticdiimide (5.4g, 0.05 equivalent) and 8.1g (0.05 equivalent) of Reichold Triepoxide were ground in a mortar with 0.4g of active chromium III tri-2-ethylhexanoate. The viscous liquid cured to a rubbery solid in 15 minutes at 200°C. No reaction was observed in the absence of COT.

Epichlorohydrin adduct of trimethylolpropane c. Reaction of Pyromelliticdiimide with Union Carbide Diepoxide 201*

Pyromelliticdiimide (5.4g, 0.05 equivalent) was ground in a mortar with 7.5g (0.5 equivalent) of Diepoxide 201 and 0.2g of active chromium III trioleate. The viscous liquid cured to a rigid solid in 15 minutes at 200°C. No reaction in the absence of active chromium III trioleate was observed.

*** Bis-cyclohexene oxide carboxylate

EXAMPLE VI

Preparation of Bis-2-Hydroxyethyl Pyromelliticdiimide

Bis-2-hydroxyethyl pyromelliticdiimide was prepared by reacting 25.0g (0.1155 mole) of pyromelliticdiimide with 10.1g (.23 mole) of ethylene oxide in the presence of 0.5g (2%) of active chromium III tri-2-ethylhexanoate in 300 ml of methylisobutylketone.

The bis-2-hydroxyethyl pyromelliticdiimide was obtained by filtration in 20.0% yield. In the absence of the catalyst no reaction was observed to take place.

EXAMPLE VII

Reaction of 4-Carboxyphthalimide with Ethylene Oxide

One mole of 4-carboxyphthalimide was reacted with two moles of ethylene oxide and a 0.4% solution of the catalyst of Example 1 in methyl isobutyl ketone at 130°C in a stainless steel pressure vessel. After 1.5 hours, the reaction appeared complete as evidenced by the absence of insoluble carboxyimide. Removal of the solvent gave a green residue which was easily crystallized from water. Repeated crystallizations from water and acetone-hexane mixtures gave a constant melting (176°–177°C), white solid. The infrared spectrum of the material revealed the presence of a hydroxyl band at 3,300 cm$^{-1}$ and the disappearance of the imide band.

EXAMPLE VIII

Reaction of Cyclopentanetetracarboxylic Diimide with Epoxy Resin

Cyclopentanetetracarboxylic diimide (CPDI) (5.2g, 0.05 equivalent), Shell Epon Resin 154 (9.0g, 0.05 equivalent) and 0.04g (0.3%) of active chromium III tri-2-ethylhexanoate (COT) were ground together in a mortar and placed in an oven at 230°C. After 5 min. a clear hard polyimide formed. The progress of the reaction was followed by infrared spectroscopy which showed disappearance of the imide N-H band and appearance of the OH band as the reaction progressed. In the absence of catalyst, gellation had not occurred in 20 min. at 230°C. After 16 hours at 230°C the uncatalyzed sample hardened but the sample was opaque due to unreacted cyclopentanetetracarboxylic diimide.

EXAMPLE IX

Reaction of Benzophenone Tetracarboxylic Diimide with Epoxy Resin

Benzophenone tetracarboxylic diimide (BTDI) (8.0g, 0.5 equivalent). Dow Epoxy Resin 332 (8.8g, 0.05 equivalent) and 0.04g (0.3%) active chromium III tri-2-ethylhexanoate were ground together in a mortar and then cured at 150°C. After 30 min. the material polymerized to a rigid mass having high strength. An uncatalyzed sample was still liquid after 8 hours at 150°C.

EXAMPLE X

Reaction of Maleimide with Epoxy Resin

Maleimide (19.4g, 0.12 equivalents), Dow Epoxy Resin 332 (35.0g, 0.2 equivalents) and 0.275g active chromium III tri-2-ethylhexanoate (0.5%) were heated in a beaker until a clear solution of the bis-2-hydroxy imide resulted. To this clear solution was added 0.055g (0.1%) of azobis-isobuteryl nitrile (AIBN). heating the resulting solution for 2 hours at 150°C provided a durable rigid polymer. In the absence of catalyst the reaction of maleimide with epoxide did not procced.

EXAMPLE XI

Reaction of Tetrahydrophthalimide with Epoxy Resin

Tetrahydrophthalimide (30.2g, 0.1 mole), Dow Epoxy Resin 332 (17.5g, 0.1 equivalent) and 0.32g active chromium III tri-2-ethylhexanoate were heated on a hot plate until formation of the bis-2-hydroxy imide occurred as noted by a clearing of the solution. To this solution was added (0.1%) of t-butyl peroxide. After heating for one hour at 150°C a hard polyimide formed, by crosslinking through the double bonds. In the absence of catalsyt, the bis-hydroxy imide did not form.

EXAMPLE XII

Reaction of 4-Carboxyphthalimide with Ethylene Oxide

Into a stainless steel bomb (90 ml) were placed 4-carboxyphthalimide (4.76g, 0.025 mole), a 0.4% solution of active chromium III tri-2-ethylhexanoate (0.18g) in methylisobutyl ketone (45 ml), and ethylene oxide (2.4g, 0.0545 mole). The bomb was sealed and placed in a 135°C oven for 4 hours with shaking at 10 minute intervals in order to insure homogeneous conditions. After cooling, the bomb was opened and the clear, green solution was evaporated to dryness under reduced pressure at 50°C. The resulting solid was triturated with ether and filtered to yield a crude product (5.0g) in 72% yield. Two recrystallizations from water and two from ethylene dichloride gave a product (2.8g) in 40% yield melting at 125°C. The chromium (III) catalyzed reaction of two moles of ethylene oxide with 4-carboxyphthalimide occurs as follows:

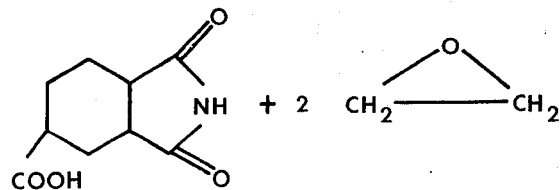 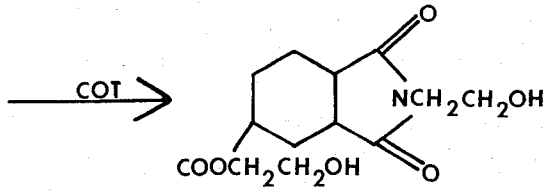

Infrared analysis revealed a hydroxyl band (3,300 cm$^{-1}$) and the disappearance of the imide band. The NMR spectrum was consistent with the bis adduct.

Anal. Calcd. for $C_{13}H_{13}NO_6$: C, 55.9; H, 4.69; N, 5.02. Found: C, 55.4; H, 4.98; N, 5.13.

EXAMPLE XIII

Reaction of 4-Carboxyphthalimide with Epoxy Resin

4-Carboxyphthalimide (191g, 1 mole), Shell Epon Resin 152, a phenol novolac containing epoxy groups, (350g, 2 equivalent) and 1.62g of active chromium III tri-2-ethylhexanoate (0.3%) were heated at 150°C for 3 hours at which time the material polymerized to a tough rigid polyesterimide. In the absence of catalyst, no reaction occurred.

EXAMPLE XIV

Reaction of Pyromellitic Diimide with Epoxy Resin

A qualitatively good product was obtained by reacting Ciba's diepoxide 1389 (a resorcinol diglycidyl ether) with pyromellitic diimide (PMDI).

Epon 152 was also reacted with pyromellitic diimide. Bulk castings showed that at 100, 125 and 150 equivalents of Epon 152/100 equivalents of pyromellitic diimide improvement in thermal stability as determined by Thermal Gravimetric Analysis was obtained. Storage of these specimens at 250°C showed that gassing was virtually non-existent.

EXAMPLE XV

Reaction of Tetrahydrophthalimide with 1,2-Propylene Oxide at 0°C in Acetone Solution.

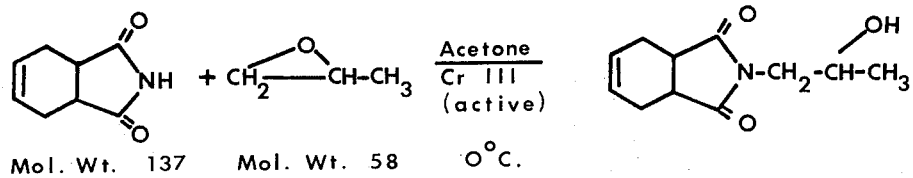

MATERIALS:
  Chromium III Tri-2-Ethylhexanoate as needed
  3.43g(0.025m) Tetrahydrophthalimide
  1.45g(0.025m) 1,2-Propylene Oxide
  Acetone to make 100 ML Solution

PROCEDURE:

Three solutions of the above composition were prepared having respectively 0, 1 and 2% Chromium III Tri-2-Ethylhexanoate. These solutions were prepared in 100 ml volumetric flasks which were kept at 0°C in an ice-water bath. Five ml aliquots were taken at various time intervals and titrated for unreacted imide with 0.25N alcoholic KOH using a pH titrimeter.

RESULTS:

| 0% Chromium III Tri-2-Ethylhexanoate | | 1% Chromium III Tri-2-Ethylhexanoate | | 2% Chromium III Tri-2-Ethylhexanote | |
|---|---|---|---|---|---|
| Elapsed Time, Min | % Imide Reacted | Elapsed Time, Min | % Imide Reacted | Elapsed Time, Min | % Imide Reacted |
| 0 | 0 | 0 | 0 | 0 | 0 |
| 50 | 0 | 40 | 2 | 40 | 9 |
| 110 | 0 | 100 | 24 | 100 | 50 |
| 155 | 0 | 145 | 34 | 145 | 59 |
| 215 | 0 | 205 | 45 | 205 | 66 |
| 275 | 0 | 265 | 47 | 265 | 69 |
| 1115 | 0 | 1105 | 66 | 1105 | 85 |
| 1300 | 0 | 1290 | 69 | 1290 | 86 |

The table above illustrates the catalytic activity of the active chromium III tri-2-ethylhexanoate, for a typical oxirane-primary cyclic imide reaction of 0° C.

A plot graphically illustrating the relationship of catalyst concentration, and the lack thereof on the above reaction is set forth below.

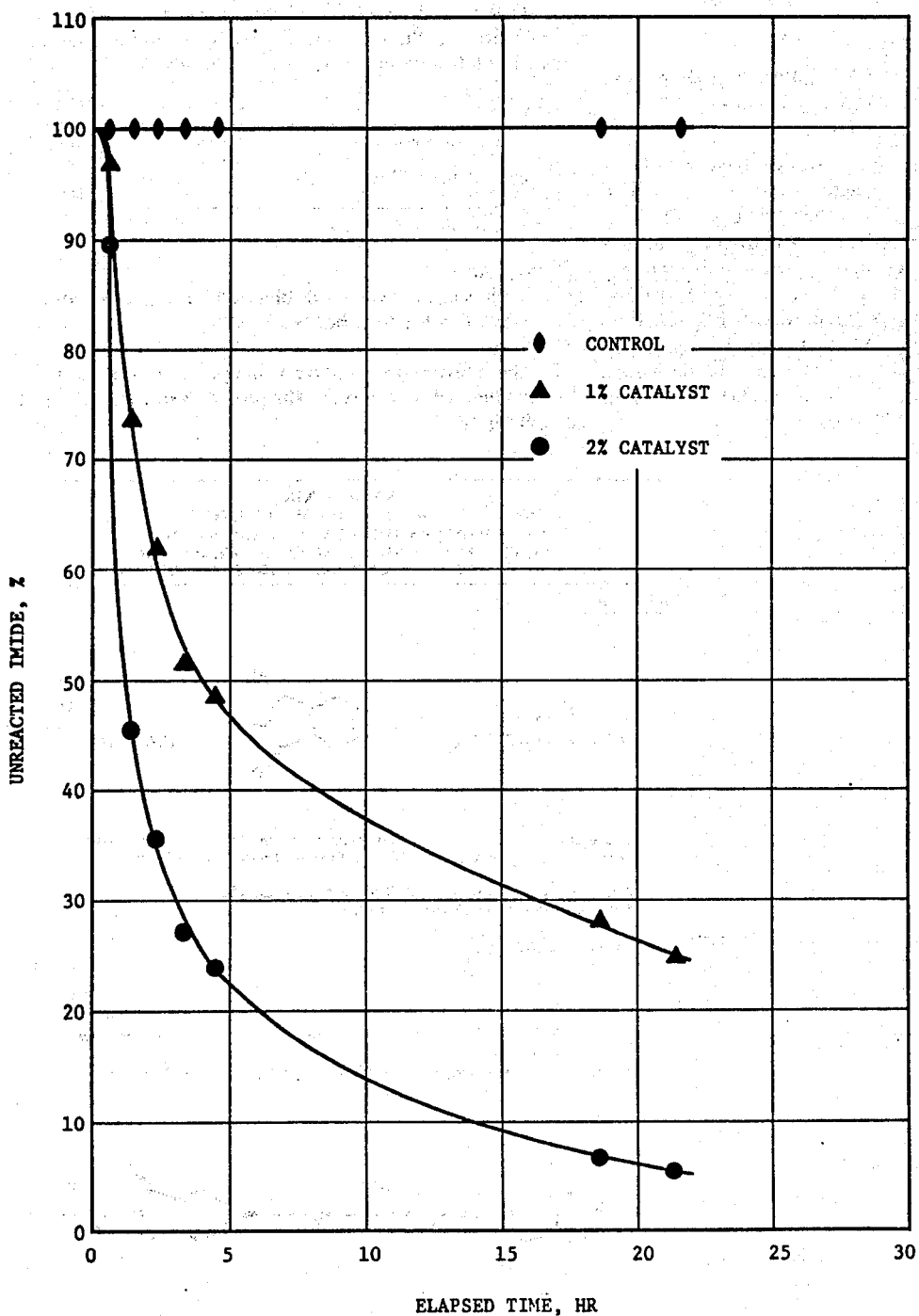

Reaction of Tetrahydrophthalimide (0.25 Molar) with 1,2-Propylene Oxide (0.25 Molar) in Acetone at 0°C

EXAMPLE XVI

Reaction of Cyclopentanetetracarboxylic Diimide with Epoxy Resin

The cyclopentanetetracarboxylic diimide when reacted with Epon 152 gave a polymer of superior thermal stability. The Thermal Gravimetric Analysis' curve indicated a 5% weight loss at slightly over 400°C.

The polymers prepared in accordance with this invention are useful in films for wire and cable wrap, motor insulation, surface coatings, lacquers, textile fibers, adhesives, molding resins, fiber glass laminates for use in radomes, aircraft leading edge structures, nose fairings, high temperature deicer ducts, and turbine compressor blades, honeycombs, bearings for use with non-lubricating liquids, with corrosive substances at elevated temperatures, in areas where lubrication is essential but inconvenient, and as retainer rings for ball bearings, electrical conductive films, when coated with tin and indium, and temperature resistant foams.

EXAMPLE XVII

Reaction of Cyclopentanetetracarboxylic Diimide with Epoxy Resin

The cyclopentanetetracarboxylic diimide when reacted with Epon 152 stoichiometrically in the presence of active chromium III tri-2-ethylhexanoate (0.3%)

gave a polymer of superior thermal stability. Thermal Gravimetric Analysis' curve indicated a 5% weight loss at slightly over 400°C for the cured polymer.

EXAMPLE XVIII
Reaction of Primary Cyclic Polyimide with Diepoxide Catalyzed with Active Chromium TRI-2-ethylhexanoate The primary cyclic polyimide was derived from Gantrez AN (low molecular weight copolymer of maleic anhydride and methyl vinyl ether, $\eta*sp$ 0.1–0.5) by first dissolving the material in excess aqueous ammonia, evaporating to dryness and cyclizing to the primary imide under vacuum (25 mm Hg) at 135°C for 48 hours. At this time the final weight was slightly less than the weight of the Gatrez AN at the beginning. Imide formation was confirmed by I.R. (infra red), showing a characteristic imide absorption at 3,200 cm$^{-1}$. This material was ground to a fine powder.

*The specific viscosity is determined on a solution of 1 gm copolymer in 100 ml of methyl isobutyl ketone at 25°C.

The following two samples were prepared to illustrate the catalytic effect of active chromium III tricarboxylates on the reaction of primary cyclic polyimides with polyfunctional oxirane compounds:

| Materials | No. 1 | No. 2 |
|---|---|---|
| Primary cyclic polyimide | 2.5 gms | 2.5 gms |
| DER 332** | 2.5 gms | 2.5 gms |
| Active Chromium III tri-2-ethylhexanoate | — | 0.1 gms |

**Diglycidyl ether of bisphenol A.

Procedure:
Each sample was well blended and placed into a 150°C oven for four hours.
Results:
The chromium catalyzed sample cured to a hard infusible solid, whereas, the uncatalyzed sample was still liquid.

EXAMPLE XIX
COMPARISON OF REACTIVITIES OF CYCLIC AND LINEAR PRIMARY IMIDES WITH OXIRANES BOTH UNCATALYZED AND CATALYZED WHEREIN THE CATALYST IS ACTIVE CHROMIUM TRI CARBOXYLATE

Reactants:

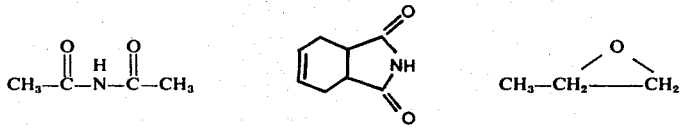

Diacetamide (Linear Primary Imide)  Tetrahydrophthalimide (Cyclic Primary Imide)  1,2-Propylene Oxide (Oxirane)

Catalyst: Active Chromium III Tri-2-Ethyl Hexanoate
Solvent: Chloroform (Spectro Grade)

Expected Reactions:

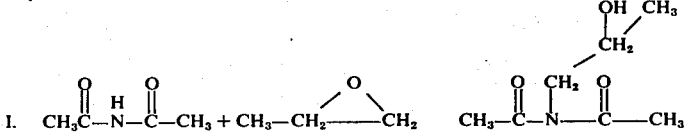

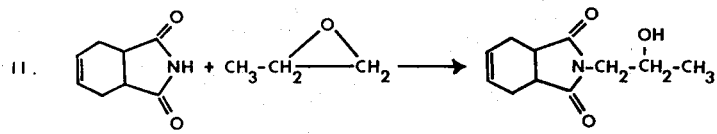

| Solutions | Ia | Ib |
|---|---|---|
| Diacetamide | 0.50g (0.005 m) | 0.50g (0.005 m) |
| 1,2-Propylene Oxide | 0.30g (0.005 m) | 0.30g (0.005 m) |
| Active Cr III Tri-2-Ethylhexanoate | — | 0.1g |
| Chloroform | To make 10 ml Total Solution | To make 10 ml Total Solution |
| | IIa | IIb |
| Tetrahydrophthalimide | 0.76g (0.005 m) | 0.76g (0.005 m) |
| 1,2-Propylene Oxide | 0.30g (0.005 m) | 0.30 g (0.005 m) |
| Active Cr III Tri-2-Ethylhexanoate | — | 0.1g |
| Chloroform | To make 10 ml Total Solution | To make 10 ml Total Solution |

Kinetic Method:

The reactions were run at 26°C. The rates were followed by infrared analysis using the characteristic absorptions for the imide >N-H (3210 cm$^{-1}$) and the alcohol —OH (3460 cm$^{-1}$). The appearance of the alcohol was used as a measure of the disappearance of the oxirane. The disappearance of the imide, of course, was measured directly.

Results:

For Solutions Ia and Ib, no apparent reaction could be detected in 140 hours at 26°C. No reaction could be detected for Solution IIa for a period of 24 hours. Solution IIb, however, was 27% complete in 5 hours and was 100% complete within 73 hours.

It is seen that when an attempt to react a typical comercially available primary linear imide with a common oxirane, which did successfully react with primary cyclic imides, in the presence of the instant catalyst, and under similar conditions, that here no apparent reaction took place.

The advantages of the present invention have been found to be obtained using any active trivalent chromium II tricarboxylate. Typical of such active chromium III compounds, prepared as described above, and commonly assigned in U.S. Pat. No. 3,819,746, the disclosure of which is incorporated by reference, are the active forms of trivalent chromium hexanoate, trivalent chromium pentanoate, trivalent chromium butyrate, trivalent chromium 2-ethylhexanoate, trivalent chromium decanoate, trivalent chromium oleate, trivalent chromium 2-octenoate, trivalent chromium toluate, trivalent chromium cresylate, trivalent chromium benzoate, trivalent chromium alkylbenzoates and trivalent chromium alkoxybenzoates.

It should also be noted that one or more than one compound of each class of epoxides may be reacted with one or more than one imide. Thus a monomeric monofunctional oxirane could be used in conjunction with a polyfunctional polymeric epoxide, for example in this reaction. Similarly mono and diimides can be utilized together.

Furthermore, the curable mixtures of the invention may be mixed at any stage prior to the completion of the degree of reaction possible as limited by the amount of one of the reactants, with fillers, plasticizers, pigments, dyestuffs, flame-inhibitors, mould lubricants or the like. Suitable extenders and fillers are, for example, asphalt, bitumen, glass fibers, mica, quartz meal, cellulose, kaolin, ground dolomite, colloidal silica having a large specific surface (Aerosil) or metal powders, such as aluminum powder.

The curable mixtures may be used in the unfilled or filled state, if desired in the form of solutions or emulsions, as laminating resins, paints, lacquers, dipping resins, molding compositions, coating compositions, pore fillers, floor coverings, potting and insulating compounds for the electrical industry, adhesives and the like, and also in the manufacture of such products.

It is to be further understood that while the oxirane compounds can be reacted with the imides throughout the range of from about 0°C to 200°C, there are certain situations wherein a particular temperature range should be utilized thus, for instance, if one of the reactants contains heat sensitive groups such as carbon to carbon double bonds temperatures over about 50°C should be avoided. The desired rate of catalysis can be achieved by the adjustment of catalyst level rather than by an increase in temperature.

Operating temperatures are determined by the temperature necessary to maintain mobility of the reactive constituents. Solvents help to maintain mobility and thereby allow low temperature reactions to be carried out. Rubbery end products are preferably prepared at temperatures below 75°C, though elevated temperatures give rise to equally satisfactory products with respect to certain physical properties.

When steel or aluminum sheets are joined to other steel or aluminum sheets with a typical oxirane-imide monomer composition which contains an active chromium III tricarboxylate, either with or without a pigment, and subjected to curing conditions (which vary with the reactants utilized), tough adhesive joints are formed. Typical compositions utilizeable herewith are those set forth in Examples XIV and XVI.

Also, organic intermediates suitable as building blocks for custom manufactured chemicals useful for plasticizers, polymers, and perhaps pharmaceuticals include the reaction products of monofunctional oxiranes with primary cyclic monoimides.

Since certain changes may be made in the above compositions and processes without departing from the scope of the invention herein involved, it is intended that all matter contained in the above description shall be interpreted as illustrative and not in a limiting sense.

We claim:

1. A method of catalyzing the reaction of primary cyclic imides with an oxirane oxygen compound which comprises carrying out the reaction in the presence of an effective catalytic amount of an active chromium III tricarboxylate having available coordination sites, at from about 0°C to 200°C.

2. A method of claim 1 wherein the reaction is carried out in a solvent system inert to the catalyst.

3. The method of claim 1 wherein the primary cyclic imide is a diimide.

4. The method of claim 1 wherein the primary cyclic imide is a diimide and the oxirane oxygen compound is a diepoxide compound.

5. The method of claim 1 wherein the primary cyclic imide is a monoimide and the oxirane oxygen compound is monofunctional as to epoxy groups.

6. The method of claim 1 wherein the primary cyclic imide is a monoimide and the oxirane oxygen compound is a diepoxide compound.

7. A method of claim 1 wherein the oxirane oxygen compound is polyfunctional and nonresinous.

8. The process of claim 1 wherein the active chromium III tricarboxylate is selected from the group consisting of active chromium III trioleate, active chromium III trihexanoate and active chromium III tritoluate.

9. The method of claim 4 wherein the reaction is carried out in a solvent system inert to the catalyst.

10. A method according to claim 2 in which the reaction is carried out at a temperature from 0° to 50°C.

11. A method according to claim 1 in which the catalyst is active chromium III 2-ethylhexanoate.

12. A method according to claim 1 in which the oxirane oxygen compound is an epoxy resin.

* * * * *

UNITED STATES PATENT OFFICE
CERTIFICATE OF CORRECTION

Patent No. 3,962,182              Dated June 8, 1976

Inventor(s) Roger B. Steele, Arthur Katzakian, Jr., Joseph J. Scigliano, and Edward E. Hamel It is certified that error appears in the above-identified patent and that said Letters Patent are hereby corrected as shown below:

Column 9 after line 50 correct the formula to

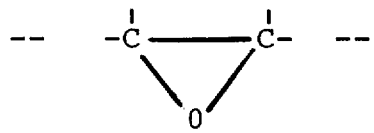

Column 11 line 39 change "doubls" to -- double --

Signed and Sealed this

Fourteenth Day of September 1976

[SEAL]

Attest:

RUTH C. MASON
Attesting Officer

C. MARSHALL DANN
Commissioner of Patents and Trademarks